US011925621B2

(12) United States Patent
Tanaka et al.

(10) Patent No.: US 11,925,621 B2
(45) Date of Patent: Mar. 12, 2024

(54) MEDICINAL PREPARATION FOR EXTERNAL USE

(71) Applicant: Sumitomo Pharma Co., Ltd., Osaka (JP)

(72) Inventors: Masayasu Tanaka, Suita (JP); Yoshihiro Oyamada, Suita (JP); Yoshinori Takada, Osaka (JP)

(73) Assignee: SUMITOMO PHARMA CO., LTD., Osaka (JP)

( * ) Notice: Subject to any disclaimer, the term of this patent is extended or adjusted under 35 U.S.C. 154(b) by 637 days.

(21) Appl. No.: 17/260,123

(22) PCT Filed: Jul. 18, 2019

(86) PCT No.: PCT/JP2019/028251

§ 371 (c)(1), (2) Date: Jan. 13, 2021

(87) PCT Pub. No.: WO2020/017585

PCT Pub. Date: Jan. 23, 2020

(65) Prior Publication Data

US 2021/0322385 A1 Oct. 21, 2021

(30) Foreign Application Priority Data

Jul. 19, 2018 (JP) ................................ 2018-136147

(51) Int. Cl.

| | |
|---|---|
| ***A61K 31/4184*** | (2006.01) |
| ***A61K 9/00*** | (2006.01) |
| ***A61K 9/06*** | (2006.01) |
| ***A61P 29/02*** | (2006.01) |

(52) U.S. Cl.

CPC ........ *A61K 31/4184* (2013.01); *A61K 9/0014* (2013.01); *A61K 9/06* (2013.01); *A61P 29/02* (2018.01)

(58) Field of Classification Search

CPC .... A61K 31/4184; A61K 9/0014; A61K 9/06; A61P 29/02

USPC ........................................................ 514/394

See application file for complete search history.

(56) References Cited

U.S. PATENT DOCUMENTS

| | | | | |
|---|---|---|---|---|
| 8,471,038 | B2 * | 6/2013 | Tsuboi .................... | A61P 13/00 544/139 |
| 2002/0169177 | A1 | 11/2002 | Kay et al. | |
| 2003/0055037 | A1 | 3/2003 | DeLombaert et al. | |
| 2011/0294804 | A1 | 12/2011 | Tsubio et al. | |

FOREIGN PATENT DOCUMENTS

| | | |
|---|---|---|
| JP | 2004-510765 | 4/2004 |
| JP | 2004-514671 | 5/2004 |
| JP | 2012-31152 | 2/2012 |
| WO | 2010/074193 | 7/2010 |

OTHER PUBLICATIONS

International Search Report dated Sep. 10, 2019 in International (PCT) Patent Application No. PCT/JP2019/028251.

International Preliminary Report on Patentability dated Jan. 19, 2021 in International (PCT) Patent Application No. PCT/JP2019/028251.

Extended European Search Report dated Mar. 15, 2022 in corresponding European Patent Application No. 19838338.2.

* cited by examiner

*Primary Examiner* — Kristin A Vajda

(74) *Attorney, Agent, or Firm* — Wenderoth, Lind & Ponack, L.L.P.

(57) ABSTRACT

The present invention pertains to a drug for the treatment and/or prevention of pain, more specifically to a medicinal preparation for external use to treat and/or prevent peripheral neuropathic pain, the medicinal preparation containing as an active ingredient $N^2$-{[1-ethyl-6-(4-methylphenoxy)-1H-benzimidazol-2-yl]methyl}-L-alaninamide.

13 Claims, No Drawings

MEDICINAL PREPARATION FOR EXTERNAL USE

TECHNICAL FIELD

The present invention relates to a medicament for the treatment and/or prevention of pain, more specifically a medicinal preparation for external use to treat and/or prevent peripheral neuropathic pain comprising $N^2$-{[1-ethyl-6-(4-methylphenoxy)-1H-benzimidazol-2-yl]methyl}-L-alaninamide as an active ingredient.

BACKGROUND ART

Peripheral nerve pain is a serious symptom in many diseases, and depending on the extent, peripheral nerve pain has a significant impact on quality of life of human, and can interfere with many kinds of general human functions.

It has been known that the mechanism of feeling peripheral nerve pain is that a signal of pain is transmitted from peripheral sensory nerves to the brain via the spinal cord, resulting in painful sensation. It has also been known that sodium channels are involved in several points of action in the pathway, and different types of sodium channels are involved depending on the points of action.

Sodium channels in the brain are Nav1.1 to Nav1.4 and Nav1.6, and those in the peripheral sensory nerves are Nav1.7 to Nav1.9. Another sodium channel which exists in the heart is Nav1.5.

As a pain medication for external use that acts on sodium channels, lidocaine formulations are commercially supplied, and have already been demonstrated to show high percutaneous absorption and the beneficial therapeutic effects on pain. It has been reported, however, to show cardiotoxic side effects, and severe restrictions are imposed on its use in clinical practice. Specifically, lidocaine is believed not only to act effectively on sodium channels in peripheral nerves, but also to effect on Nav1.5 which affects the heart. In addition, it is believed that even topical administration of lidocaine in external use can affect channels in the heart which exists deeply inside the body. Generally, such side effects have made it difficult to develop a pain medication which utilizes a sodium channel, and especially, it has been a major challenge to obtain the selectivity of channels.

A research team including the present inventors has revealed that a bicyclic heterocyclic compound with a specific structure has an analgesic effect, and inhibits a sensory neuron-specific Na channel (SNS) in a peripheral nerve (Patent Literature 1).

Patent Literature 1, however, discloses only in vitro studies for evaluating effects on Na channels, and it does not disclose any consideration about pharmacokinetic effects including percutaneous absorption. In order to realize the application to topical administration at a peripheral site, it was necessary to examine pharmacokinetic effects in view of the efficiency of percutaneous absorption and metabolism, and to study the applicability to formulations suitable for topical administration and the stability of formulations. Considering the possibility of the above side effects of lidocaine, it was also necessary to examine the selectivity of sodium channels. In the examination of them, it was not easy to select some applicable compounds among a number of compounds disclosed in Patent Literature 1, and to reduce the side effects while conferring the selectivity of sodium channels.

CITATION LIST

Patent Literature

[Patent Literature 1] WO 2010/074193

SUMMARY OF INVENTION

Problems to be Solved by the Invention

An object of the present invention is to provide a medicinal preparation for external use to treat peripheral neuropathic pain.

Means of Solving the Problems

The present inventors have extensively studied to achieve the present invention, and then have found that, among various compounds disclosed in Patent Literature 1, $N^2$-{[1-ethyl-6-(4-methylphenoxy)-1H-benzimidazol-2-yl]methyl}-L-alaninamide is suitable for a medicinal preparation for external use in terms of percutaneous absorption, and the medicinal preparation also has a good property in the stability for the preservation. The present inventors have also found that the medicinal preparation has an analgesic effect that is comparable with an ointment formulation of lidocaine, which is an existing analgesic formulation, and that surprisingly, the medicinal preparation has the remarkable stability far beyond the lidocaine formulation in terms of reduction of side effects concerning the cardiovascular system.

The present invention is described as follows:

Item 1.

A pharmaceutical composition for external use comprising $N^2$-{[1-ethyl-6-(4-methylphenoxy)-1H-benzimidazol-2-yl]methyl}-L-alaninamide or a pharmaceutically acceptable salt thereof as an active ingredient.

Item 2.

The composition according to Item 1, further comprising an external base which comprises at least one selected from the group consisting of petrolatum (e.g., white or yellow), gelled hydrocarbons (e.g., Plastibase (trademark)), paraffins (e.g., liquid paraffin), lanolin, hydrous lanolin, lanolin alcohol, polyethylene glycol, silicon, waxes (e.g., beeswax), vegetable oil, lard, squalane, and simple ointment.

Item 3.

The composition according to Item 1 or 2, wherein the active ingredient is comprised in the range of 0.01% (w/v)-10% (w/v).

Item 4.

The composition according to any one of Items 1 to 3, which is substantially free from water.

Item 5.

The composition according to any one of Items 1 to 4, wherein the pharmaceutical composition for external use is in the dosage form of an embrocation, patch, or spray (or aerosol).

Item 6.

The composition according to Item 5, wherein the embrocation is an ointment.

Item 7.

The composition according to any one of Items 1 to 6, for use in the treatment and/or prevention of pain.

Item 8.

The composition according to Item 7, wherein the pain is peripheral neuropathic pain.

Item 9.

The composition according to any one of Items 1 to 8, wherein the active ingredient is comprised in such an amount that 0.1 mg or more of the active ingredient can be administered at a time in topical external administration.

Effect of the Invention

The medicinal preparation for external use of the present invention is expected as a useful medicament for the treatment of pain because it has a good percutaneous absorption property and a good stability for the preservation, exhibits a good analgesic effect comparable with an existing external medicine of lidocaine in topical administration, and has less effect on the heart, and thus, the dissociation between the analgesic effect and side effects on the heart is larger than those of the external medicine of lidocaine.

DESCRIPTION OF EMBODIMENTS $N^2$-{[1-Ethyl-6-(4-methylphenoxy)-1H-benzimidazol-2-yl]methyl}-L-alaninamide of the present invention (hereinafter, referred to as "the present compound") is a compound disclosed in Patent Literature 1.

A pharmaceutically acceptable salt in the present invention includes a salt formed with a basic functional group in the above present compound and an acid. Examples of the pharmaceutically acceptable salt include hydrochloride, hydrobromide, sulfate, nitrate, acetate, trifluoroacetate, methanesulfonate, toluenesulfonate, and citrate.

The term "pain" used herein refers to a pain sensed by a peripheral nerve, and the present invention can be used as a medicament for the treatment and/or prevention of pain involving peripheral nerve such as C fiber and Δδ fiber; spontaneous pain such as numbness, burning sensation, dull pain, pricking pain, and shooting pain; neuropathic pain accompanied by hyperalgesia to mechanical or heat and cold stimulation or by allodynia; nociceptive pain; inflammatory pain; small fiber neuropathy; erythromelalgia; or paroxysmal extreme pain disorder, etc. The term "neuropathic pain" used herein includes, for example, diabetic neuropathy, postherpetic neuralgia, chemotherapy-induced neuropathy, cancer pain, sensory nerve damage caused by viral infection in human immunodeficiency syndrome, trigeminal neuralgia, complex regional pain syndrome, reflex sympathetic dystrophy, neuralgia after low back surgery, phantom limb pain, pain after spinal cord injury, persistent postoperative pain, inflammatory demyelinating polyradiculoneuropathy, alcoholic neuropathy, entrapment peripheral neuropathy, iatrogenic neuropathy, sudden sensorineural disorder, malnutrition-induced neuropathy, radiation-induced neuropathy, radiculopathy, toxic peripheral neuropathy, traumatic peripheral neuropathy, brachial plexus avulsion injury, glossopharyngeal neuralgia, autoimmune neuropathy, chronic cauda equina syndrome, pain in extremity, and erythromelalgia. Nociceptive pain or inflammatory pain includes low back pain, back pain, abdominal pain, chronic rheumatoid arthritis, pain due to osteoarthritis, muscular pain, acute postoperative pain, fracture pain, and pain after burn injury. In addition, the present compound and a pharmaceutically acceptable salt thereof can be used as a medicament for the treatment or prevention of dysuria. The term "dysuria" used herein includes frequent urination, bladder pain caused by prostatic hyperplasia.

For the enhancement of its action, the present compound may be used in combination with, for example, a non-steroidal anti-inflammatory agent such as celecoxib, ibuprofen, loxoprofen, acetaminophen, and diclofenac; a steroidal anti-inflammatory agent such as dexamethasone and prednisolone; and an opioid analgesic agent such as tramadol, morphine, and oxycodone. The present compound may also be used in combination with an antiepileptic agent such as pregabalin and carbamazepine, an aldose reductase inhibitor such as epalrestat, an prostaglandin derivative drug such as limaprost alfadex, an antidepressant agent such as amitriptyline and duloxetine, an anticonvulsant agent, an antianxiety agent, a dopamine receptor agonist, an antiparkinsonian agent, a hormone preparation, a migraine medication, a beta-adrenergic receptor antagonist, an anti-dementia agent, and an mood-disorder amelioration agent. A preferable agent combined with the present compound and a pharmaceutically acceptable salt thereof includes an antiepileptic agent such as pregabalin and carbamazepine, an antidepressant agent such as amitriptyline and duloxetine, a narcotic analgesic agent such as morphine, oxycodone, and tramadol, an anti-inflammatory agent such as acetaminophen, diclofenac, and dexamethasone, an aldose reductase inhibitor such as epalrestat, and a prostaglandin derivative such as limaprost alfadex. The present compound may also be combined with an agent such as an antiemetic agent and a sleep-inducing agent in order to reduce side effects. The present compound and a concomitant drug for the combination use may be administered at any appropriate time, and may be administered to a subject of the treatment at the same time, or with any appropriate intervals. The present compound may be formulated into a single unit dosage form with the concomitant drug, or the present compound and the concomitant drug are administered in separate formulations or via separate administration routes. The dose of concomitant drug may be optionally selected on the basis of the dose for clinical use. The ratio of the present compound and the concomitant drug may be optionally selected depending on a subject of the treatment, a route of administration, a targeted disease, symptoms, and combination thereof. When a subject of the treatment is a human, 0.01 to 1000 parts by weight of a concomitant drug may be used to 1 part by weight of the present compound.

The term "pharmaceutical composition for external use" used herein refers to a composition in which a medicinal component affects directly a diseased site of pain by percutaneous or transmucosal administration, having a dosage form of an embrocation, a patch, or a spray (or aerosol). Examples of the embrocation include a plaster, an ointment, a cream, a gel, a liniment, and a lotion, and examples of the patch include a cataplasm, a tape, a poultice, and a plaster. Preferably, the composition includes an embrocation, a patch, and a spray (or aerosol) which have a low water content.

The present composition is a liquid or semisolid composition as an embrocation, or a semisolid or solid composition as a patch, or a composition in the form of a mist, powder, foam, or paste as a spray (or aerosol). In terms of the stability for the preservation of the present compound, the composition preferably has a low water content. It is preferable, but not limited to, that the water content of the composition is 5% or less to the total mass of the composition, more preferably 3% or less, still more preferably 1% or less, still more preferably 0.5% or less, and still more preferably 0.1% or less. The term "substantially free from water" used herein means less than or equal to the water content such that water does not significantly affect the stability for the preservation of the present compound. Specifically, it is preferable that the water content of the composition is 5% or less to the total mass of the composition, more preferably 3% or less, still more preferably 1% or less, still more preferably 0.5% or less, and still more preferably 0.1% or less.

The embrocation of the pharmaceutical composition for external use herein includes, specifically, a liquid or semi-solid composition such as a plaster, an ointment, a cream, a gel, a liniment, or a lotion, and an ointment having a low water content is preferable. The ointment includes an oral ointment and an ophthalmic ointment.

A solvent or base comprised in the composition of the present invention is not particularly limited to its type or property, and may be hydrophilic or hydrophobic such as oleaginous, and may be used with optionally mixing or emulsifying with different plural kinds of solvents or bases. The solvent or base includes, for example, petrolatum (e.g., white or yellow), gelled hydrocarbons (e.g., Plastibase (registered trademark)), paraffins (e.g., liquid paraffin), lanolin, hydrous lanolin, lanolin alcohols, polyethylene glycol, silicon, waxes (e.g., beeswax), vegetable oils, lard, squalane, and simple ointments for oleaginous components, and includes water, glycerol, propylene glycol, 1,3-butylene glycol, ethanol, and isopropanol for aqueous components. The solvent or base herein is preferably oleaginous.

The content of the present compound or a pharmaceutically acceptable salt thereof in the embrocation is preferably, but not limited to, 0.01 to 10% by weight, more preferably 0.1 to 6% by weight, and especially preferably 0.3 to 3% by weight.

The embrocation composition herein may comprise additives which are used in the pharmaceutical field and cosmetic field, depending on the dosage form or a route for administration of the composition, as well as the above solvent or base. Such additives include, for example, gelling agents, alcohols, polyhydric alcohols, oils, waxes, hydrocarbons, fatty acids, fatty acid esters, emulsifiers, solubilizers, pH regulators, antioxidants, flexibilizers, thickeners, moisturizers, preservatives, stabilizers, flavors, and transdermal absorption enhancers. Specifically, the alcohols include, for example, benzyl alcohol, cetyl alcohol, lauryl alcohol, decanol, oleyl alcohol, octyldodecanol, and octyl alcohol. The polyhydric alcohols include, for example, ethylene glycol, diethylene glycol, polyethylene glycol, propylene glycol, polypropylene glycol, glycerol, and 1,3-butylene glycol. The oils include, for example, sesame oil, soybean oil, castor oil, and olive oil. The waxes include, for example, polyoxyethylene sorbitol beeswax, microcrystalline wax, and cetanol-monostearate polyethylene glycol mixed wax. The hydrocarbons include, for example, squalane, squalene, and liquid paraffin. The fatty acids include, for example, oleic acid, behenic acid, myristic acid, stearic acid, and isostearic acid. The fatty acid esters include, for example, isopropyl myristate, diisopropyl adipate, diethyl sebacate, and octyldodecyl myristate. The emulsifiers include, for example, polyoxyethylene alkyl ether, polyoxyethylene hydrogenated castor oil, sorbitan fatty acid ester, glycerolfatty acid ester, and alkyl glyceryl ether. The solubilizers include, for example, isopropanol, oleic acid, ethyl oleate, polysorbate 80, anhydrous ethanol, and nicotinamide. The pH regulators include, for example, hydrochloric acid, sodium hydroxide, meglumine, phosphoric acid, succinic acid, maleic acid, triisopropanolamine, and monoethanolamine. The antioxidants include, for example, 2-mercaptobenzimidazole, palmitoyl-L-ascorbic acid, 3(2)-t-butyl-4-methylphenol, propyl gallate, α-tocopherol, 1,3-butylene glycol, benzotriazole, L-ascorbic acid, sodium metabisulfite, sodium sulfite, sodium thiosulfate, sodium hydrogen sulfite, and sodium edetate. The flexibilizers include, for example, liquid paraffin, purified lanolin, squalane, squalene, olive oil, sesame oil, camellia oil, persic oil, peanut oil, isopropyl myristate, oleyl oleate, diisopropyl adipate, and medium chain fatty acid triglyceride. The preservatives include, for example, alkyl parahydroxybenzoate, benzoic acid, and sodium benzoate. The thickeners include, for example, celluloses such as methyl cellulose, hydroxyethyl cellulose, hydroxypropyl cellulose, hydroxypropylmethyl cellulose, nitrocellulose, and cationic cellulose, xanthan gum, guar gum, cationic guar gum, starch, cationic starch, sodium hyaluronate, alginic acid, carrageenan, carboxyl vinyl polymer, polyacrylic acid, polyvinyl alcohol, polyethylene glycol, and polypropylene glycol. The stabilizers include, for example, L-aspartate, L-arginine, L-leucine, L-methionine, sodium benzoate, ethanol, sodium edetate, ammonium chloride, sodium chloride, citric acid, sodium citrate, glycine, sesame oil, sodium acetate, zinc oxide, diethanolamine, tartaric acid, stearic acid, D-sorbitol, D-mannitol, sodium bicarbonate, urea, glycerol, white soft sugar, glucose, propylene glycol, polysorbate 80, and macrogol 400. The flavors include, for example, 1-menthol, dl-menthol, mentha oil, eucalyptus oil, lavender oil, rose oil, and orange oil. The transdermal absorption enhancers include, for example, acetic acid, lactic acid, citric acid, malic acid, butyl acetate, ethyl lactate, cetyl lactate, propylene carbonate, crotamiton, N-methyl-2-pyrrolidone, triacetin, medium chain fatty acid triglyceride, medium chain fatty acid diglyceride, medium chain fatty acid monoglyceride, methyl isobutyl ketone, triethanolamine, lecithin, and polybutylene.

The spray (or aerosol) composition herein comprises a formulation component such as a vehicle in which a drug is to be dissolved, alcohols that increase the effect of percutaneous or transmucosal absorption when a drug is sprayed and enhance the solubility of the drug, a thickener for maintaining the particle size of a drug when sprayed, and a propellant for spraying a solution comprising a drug.

Representative examples of the above propellant include liquefied gas such as LPG (i.e., liquefied petroleum gas which mainly comprises propane, i-butane, and n-butane), n-pentane, i-pentane, dimethyl ether, and CFC substitutes for chlorofluorocarbon such as 1,1,1,2-tetrafluoroethane and 1,1-difluoroethane, and they may be used alone or in combination with two or more of them. The above liquefied gas may also be combined with compressed gas such as air, nitrogen, oxygen, carbon dioxide, and nitrogen monoxide.

Representative examples of the above thickener includes celluloses such as methyl cellulose, hydroxyethyl cellulose, hydroxypropyl cellulose, hydroxypropylmethyl cellulose, nitrocellulose, and cationic cellulose, xanthan gum, guar gum, cationic guar gum, starch, cationic starch, sodium hyaluronate, alginic acid, carrageenan, carboxyl vinyl polymer, polyacrylic acid, polyvinyl alcohol, polyethylene glycol, and polypropylene glycol, and they may be used alone or in combination with two or more of them.

Representative examples of the above alcohols preferably include monovalent lower alcohols and polyhydric alcohols. Representative examples of the monovalent lower alcohols include alcohols with 2 to 4 carbon atoms such as ethanol, denatured ethanol, n-propanol, i-propanol, n-butanol, and i-butanol. Examples of the polyhydric alcohols include ethylene glycol, diethylene glycol, polyethylene glycol, propylene glycol, polypropylene glycol, glycerol, and 1,3-butylene glycol.

The patch herein comprises a backing and an adhesive layer that is laminated on at least one side of the backing, and the adhesive layer comprises the present compound or a pharmaceutically acceptable salt thereof, and formulation components such as a flexibilizer, a tackifier, and an absorption promoter.

The present compound or a pharmaceutically acceptable salt thereof is comprised in the adhesive layer of the patch herein in the amount of, but not limited to, 30 to 80% by weight, and preferably 40 to 70% by weight of the total mass of the adhesive layer of the patch herein.

Preferably, the patch comprises at least one selected from the group consisting of liquid paraffin, squalane, isopropyl myristate, olive oil, camellia oil, persic oil, and peanut oil as the flexibilizer. The blending amount of the flexibilizer is preferably 1 to 70% by weight of the total mass of the adhesive layer.

Preferred examples of the tackifier include, but not limited to, alicyclic saturated hydrocarbon resins (e.g., petroleum resins), terpene resins, rosin resins, rosin ester resins, and oil-soluble phenol resins.

The absorption promoter may be a compound that shows the promotion effect of absorption at skin, and preferable examples include, but not limited to, fatty acid, aliphatic alcohol, fatty acid ester, fatty acid ether, aromatic organic acid, aromatic alcohol, aromatic organic acid ester, and aromatic organic acid ether.

The patch herein may also optionally comprise other additives such as a crosslinking agent, a preservative, and a filler.

The backing may be a backing that is generally used for patches, and materials used for the backing preferably include, but not limited to, polyesters such as polyethylene terephthalate (PET), polybutylene terephthalate, and polyethylene naphthalate; polyolefins such as polyethylene and polypropylene; nylons; polycarbonates; and metals such as aluminium. The backing is preferably used in the form of films, fabrics, foils, and porous sheets, or a laminated form of them.

The patch herein may be coated with a release liner on the opposite side of the backing of the adhesive layer. Such release liner is a release film to coat and protect the adhesive layer, and may be one generally used for patches, and is not limited. Examples of such release liner include materials such as resin films including polyester (for example, polyethylene terephthalate, polyethylene naphthalate, and polybutylene terephthalate) and polyolefin (for example, polyethylene and polypropylene); paper; and cellulose derivatives. Preferably, the side that abuts on the adhesive layer is coated with silicone or Teflon (Registered Trademark), and processed with mold release. In particular, a polyethylene terephthalate film that is processed with silicone is preferable.

Generally, the adhesive layer in the patch herein has preferably, but not limited to, 30 to 500 μm thick, more preferably 40 to 300 μm thick, and still more preferably 50 to 200 μm thick.

EXAMPLES

Hereinafter, the present invention is illustrated with Examples, Comparative examples, and various Tests, but the present invention is not limited thereto.

In the following Examples, the present compound of $N^2$-{[1-ethyl-6-(4-methylphenoxy)-1H-benzimidazol-2-yl]methyl}-L-alaninamide is abbreviated as "Compound A".

Ointment formulations were prepared in the following Examples 1 to 6 and Comparative example 1, and patch formulations were prepared in Examples 7 and 8, and a gel formulation was prepared in Example 9.

Example 1

1% by weight of Compound A was added to 7% by weight of oleic acid, and the mixture was mixed to be dissolved. 92% by weight of white petrolatum was added thereto, and the mixture was uniformly mixed and kneaded to form an ointment formulation.

Example 2

1% by weight of Compound A was added to 7% by weight of oleic acid, and the mixture was mixed to be dissolved. 91% by weight of white petrolatum and 1% by weight of water for injection were added thereto, and the mixture was uniformly mixed and kneaded to form an ointment formulation.

Example 3

1% by weight of Compound A was added to 7% by weight of oleic acid, and the mixture was mixed to be dissolved. 89% by weight of white petrolatum and 3% by weight of water for injection were added thereto, and the mixture was uniformly mixed and kneaded to form an ointment formulation.

Example 4

1% by weight of Compound A was added to 7% by weight of oleic acid, and the mixture was mixed to be dissolved. 87% by weight of white petrolatum and 5% by weight of water for injection were added thereto, and the mixture was uniformly mixed and kneaded to form an ointment formulation.

Comparative Example 1

1% by weight of Compound A was added to 7% by weight of oleic acid, and the mixture was mixed to be dissolved. 82% by weight of white petrolatum and 10% by weight of water for injection were added thereto, and the mixture was uniformly mixed and kneaded to form an ointment formulation.

Example 5

1% by weight of Compound A was added to 7% by weight of oleic acid, and the mixture was mixed to be dissolved. 92% by weight of gelled hydrocarbon was added thereto, and the mixture was uniformly mixed and kneaded to form an ointment formulation.

Example 6

6% by weight of Compound A was added to 44% by weight of oleic acid, and the mixture was mixed to be dissolved. 50% by weight of gelled hydrocarbon was added thereto, and the mixture was uniformly mixed and kneaded to form an ointment formulation.

Example 7. Preparation of a Patch Formulation (Preparation of a Rubber-Based Adhesive Agent)

0.5 g of polyisobutylene (Oppanol N-100: BASF SE), 0.24 g of liquid paraffin (HICALL M-352; KANEDA Co., Ltd), 0.3 g of polybutene (Nisseki Polybutene HV-300F; JXTG Energy Corporation), and 0.6 g of alicyclic saturated hydrocarbon resin (Arkon P-100; Arakawa Chemical Industries, Ltd.) were dissolved in 6 mL of tetrahydrofuran to obtain an adhesive layer.

0.02 g of Compound A was added to 0.14 g of oleic acid, and after dissolution was confirmed, 0.2 g of isopropyl myristate was added thereto. The adhesive layer prepared above was added thereto, and the mixture was well stirred to obtain a mixed solution. The obtained mixture was extended on a backing and dried at room temperature for a day so that the adhesive layer had about 60 μm thick after drying. Then, a release liner was attached thereto to provide a tape formulation. The content of Compound A in the formulation was 1% by weight.

50.8 μm of polyethylene terephthalate from 3M Healthcare Company and/or an ethylene-vinyl acetate copolymer laminate film (Scotchpak #9732) were used as a backing. Bynasheet 64S-018B from Fujimori Kogyo Co., Ltd. was used as a release liner.

Example 8. Preparation of a Patch Formulation (Preparation of an Acryl-Based Adhesive Agent)

0.854 g of an acryl-based adhesive agent (DURO-TAK 387-2287, Henkel AG & Co. KGaA, 51% by weight of solid content), 0.3 mL of ethyl acetate, and oleic acid were mixed, so that the content ratio of oleic acid was 10% in an adhesive layer. To this mixture was added Compound A dissolved in 0.4 mL of methanol so that the content of Compound A was 3% in the adhesive layer. The mixture was sufficiently stirred to obtain a mixture. The obtained mixture was extended on a backing and dried at room temperature for a day so that the adhesive layer had about 60 μm thick after drying. Then, a release liner was attached thereto to provide a tape formulation.

Example 9. Preparation of a Gel Formulation

1% by weight of Compound A was added to 7% by weight of oleic acid, and the mixture was mixed to be dissolved. To the mixture were added 6.4% by weight of hydrogenated soybean phospholipids (LECINOL S-10; Nikko Chemicals Co., Ltd), 27.6% by weight of medium chain fatty acid triglyceride (Triester F-810; Nikko Chemicals Co., Ltd), 4.6% by weight of glyceryl triisooctanoate (Trifat S-308; Nikko Chemicals Co., Ltd), 12.9% by weight of octyldodecyl myristate (ODM-100; Nikko Chemicals Co., Ltd), 5.5% by weight of microcrystalline wax (purified microcrystalline wax; Nikko Rika Corporation), 3.0% by weight of dextrin palmitate (dextrin palmitate N; Nikko Chemicals Co., Ltd), 2.0% by weight of monostearyl glyceryl ether (batyl alcohol EX; Nikko Chemicals Co., Ltd), 25.0% by weight of white petrolatum, and 8.0% by weight of liquid paraffin. The mixture was uniformly dispersed at ordinary temperature, warmed to 90° C., and stirred to be dissolved. Then, the mixture was filled into a container and cooled to obtain a gel formulation.

Control Example 1

To 7% by weight of oleic acid was added 93% by weight of white petrolatum, and the mixture was uniformly mixed and kneaded to form an ointment formulation.

Test 1. Test for the Stability for the Preservation of Ointment Formulations

Accelerated stability tests were conducted for ointment formulations obtained in Examples 1 to 4 and Comparative example 1. A polypropylene pot for ointment with a capacity of 6 mL was filled with about 5 g of each ointment formulation immediately after preparation, and stored under 60° C. For drug contents after storage, ointment formulations were weighed from ointment pots: 2 mL of tetrahydrofuran was added thereto, and the mixture was stirred; 2 mL of 50% methanol solution was further added thereto, and the mixture was stirred; and the mixture was separated by centrifugation, and the obtained aqueous layer was measured by HPLC.

(HPLC Conditions)

Column: Gemini/NX-C18 3 μm (4.6φ×100 mm)
Mobile phase A: 10 mM Phosphoric acid buffer (pH 7.4)
Mobile phase B: acetonitrile
Column temperature: 30° C.
Flow rate: 2.0 mL/min
Detector: Ultraviolet absorptiometer (measurement wavelength: 220 nm)
Supply of mobile phases: The concentration gradient was controlled by changing the mixing ratio of mobile phase A and mobile phase B as follows:

| Time after injection (min) | Mobile phase A (%) | Mobile phase B (%) |
|---|---|---|
| 0-17.5 | 65 to 30 | 35 to 70 |
| 17.5-37.5 | 30 | 70 |
| 37.5-38 | 30 to 65 | 70 to 35 |
| 38-48 | 65 | 35 |

The contents of drug remaining after the preservation are shown in the following table:

Results of test for the stability for the preservation of ointment formulations (the contents of drug remaining after the preservation at 60° C.)

| | Example 1 | Example 2 | Example 3 | Example 4 | Comparative Example 1 |
|---|---|---|---|---|---|
| 1-week preservation | 98.5 | 96.2 | 95.8 | 94.7 | 93.8 |

Test 2. Measurement of the Analgesic Effect in a Fifth Lumbar Nerve Ligation Model Inhibitory effects of Compound A and lidocaine on neuropathic pain were confirmed with evaluation of the analgesic effect in a fifth lumber nerve ligation (SNL: spinal nerve litigation) model.

A SNL model was prepared by a method of Kim and Chung (Pain 50, 355-363, 1992) with partial modification thereof. Specifically, male 5-week-old Wistar rats were anesthetized with pentobarbital and isoflurane inhalation, and under anesthesia, an unilateral fifth lumber nerve was exposed. Then, the fifth lumber nerve was ligated with a silk surgical suture to obtain a SNL model.

Evaluation of the analgesic effect was conducted with the von Frey test. Specifically, an animal was poked with a von Frey hair on a footpad in a hind limb of an animal at the side of operation. Reaction thresholds (50% paw withdrawal thresholds) to mechanical stimulation were calculated with a formula according to a method of Chaplan (Journal of Neuroscience Methods 53, 55-63, 1994).

From 7 days after the preparation of a SNL model, it was observed by a preliminary study that reaction thresholds of a hind limb at the side of operation were significantly decreased in animals. Accordingly, the analgesic effect of test compounds was evaluated at any one day from 7 days to 10 days after the SNL surgery. Reaction thresholds were measured on one and two days before the evaluation of test compounds, and an average of the measured values was determined as the reaction threshold before administration of test compounds.

Animals were divided in three groups (n=9) so that there was a small difference in the average value of the reaction thresholds of each group before administration of test compounds, and each group had a small variation of the reaction thresholds. One day after the division into groups, test compounds were administered. The ointment formulation of Example 1 was used for a group treated with Compound A, 5% lidocaine ointment (United States Pharmacopeia), which can be purchased from Taro Pharmaceuticals U.S.A., Inc. in the United States, was used for a group treated with lidocaine, and the ointment formulation of Control example 1 was used for a group treated with a vehicle. Administration of a test compound was carried out by application of about 10 mg of each formulation on a medical adhesive film, and attachment of the film to a footpad of a SNL rat at the side of operation under anesthesia with isoflurane inhalation. One hour after the application, the film was removed, and another one hour after, reaction thresholds after administration of the test compound were evaluated. After the evaluation, blood was immediately collected from a cervical vein, and the concentration of the test compound in plasma was measured.

The efficacy of the analgesic effect of a test compound is shown as an extension range of reaction thresholds±standard error (g) by the following formula: (Reaction threshold after administration of a test compound)−(Reaction threshold before administration of a test compound).

(Test Results)

Extension ranges of reaction thresholds of groups treated with a vehicle, Compound A, and lidocaine were 0.0±0.37 g, 2.2±0.56 g, and 4.1±0.62 g, respectively. The extension ranges of reaction thresholds of groups treated with Compound A and lidocaine were statistically significantly increased, compared with that of a group treated with a vehicle. There was, however, no statistically significant difference between the extension ranges of reaction thresholds of groups treated with Compound A and lidocaine. The concentrations of Compound A and lidocaine in plasma were 25.2 ng/mL and 132.6 ng/mL, respectively.

The above results showed that Compound A in the ointment formulation of Example 1 was percutaneously absorbed, and a good analgesic effect was exhibited in SNL model rats, which are a pathological animal model. The analgesic effect was comparable to that of a lidocaine formulation.

Test 3. Safety Pharmacology Study of the Cardiovascular System

Effect of Compound A or lidocaine to the cardiovascular system was studied from effects on ECG (electrocardiogram) parameters of guinea pigs under anesthesia. Evaluation of ECG of guinea pigs was conducted under anesthesia with intra-abdominal administration of a mixed solution of urethane and α-chloralose. Guinea pigs under anesthesia were retained in a supine position, and a right cervical vein was exposed to indwell a cannula. A solvent prepared with 20% polyethylene glycol 400, 10% dimethylformamide, 10% ethanol, and 0.6% lactic acid was used for a solvent in which a test compound was to be dissolved. Compound A dissolved in a solvent at a dose of 30 mg/kg, lidocaine dissolved in a solvent at a dose of 15 mg/kg, or a solvent was continuously intravenously administered via a cannula at a constant rate for 30 minutes. In connection with the efficacy of the effect of lidocaine on ECG, PR interval is shown as a rate of change (%) by the following equation:

{(PR interval 30 minutes after administration)−(PR interval before administration)}/(PR interval before administration)×100. QRS interval and QTc interval are shown as rates of change (%) by similar equations.

10 minutes, 20 minutes, and 30 minutes after administration was started, blood was collected from a left cervical vein, and the concentrations of Compound A and lidocaine in plasma were measured.

(Test Results)

In the vehicle group, PR interval was prolonged for 15.2%, QRS interval was prolonged for 8.4%, and QTc interval was prolonged for 6.0% at 30 minutes after administration.

In the lidocaine group, PR interval was prolonged for 35.1%, QRS interval was prolonged for 44.5%, and QTc interval was prolonged for 15.8% at 30 minutes after administration. There was a statistically significant difference between the rates of change of each parameter in the lidocaine group and that in the vehicle group. The maximum concentration of lidocaine in plasma at a dose of 15 mg/kg was 3.57 μg/mL.

In the Compound A group, PR interval was prolonged for 22.3%, QRS interval was prolonged for 10.3%, and QTc interval was prolonged for 9.0% at 30 minutes after administration. There was no statistically significant difference between the rates of change of each parameter in the Compound A group and that in the vehicle group. The maximum concentration of Compound A in plasma at a dose of 30 mg/kg was 16.9 μg/mL.

From the above results, effect of Compound A on the cardiovascular system was not observed until the dose rose to 30 mg/kg. On the other hand, effect of lidocaine on ECG parameters was observed at a dose of 15 mg/kg.

Combined with the results in the drug efficacy model, Compound A was not observed to affect the cardiovascular system even when its concentration in plasma was about 670 times higher than that at which the analgesic effect was appeared. On the other hand, lidocaine was observed to affect ECG parameters when its concentration in plasma was about 27 times higher than that at which the analgesic effect was appeared. Thus, it was found that Compound A has higher level of safety than lidocaine does.

The invention claimed is:

1. A pharmaceutical composition for external use comprising $N^2$-{[1-ethyl-6-(4-methylphenoxy)-1H-benzimidazol-2-yl]methyl}-L-alaninamide or a pharmaceutically acceptable salt thereof as an active ingredient, wherein the composition is substantially free from water.

2. The composition according to claim 1, further comprising an external base comprising at least one selected from the group consisting of white petrolatum, yellow petrolatum, a gelled hydrocarbon, a paraffin, lanolin, hydrous lanolin, a lanolin alcohol, polyethylene glycol, silicon, a wax, a vegetable oil, lard, squalane, and a simple ointment.

3. The composition according to claim 1, wherein the composition comprises the active ingredient in an amount of 0.01% (w/v)-10% (w/v).

4. The composition according to claim 1, wherein the composition comprises an amount of water of 5% or less based on a total mass of the composition.

5. The composition according to claim 1, wherein the composition is in a dosage form of an embrocation, a patch or a spray.

6. The composition according to claim 5, wherein the embrocation is an ointment.

7. The composition according to claim 1, for use in the treatment and/or prevention of pain.

8. The composition according to claim 7, wherein the pain is peripheral neuropathic pain.

9. The composition according to claim 1, wherein the composition comprises the active ingredient in an amount such that 0.1 mg or more of the active ingredient can be administered at a time in topical external administration.

10. A method of treating or preventing pain, comprising administering the composition according to claim 1 to a subject in need thereof.

11. The method according to claim 10, wherein the pain is peripheral neuropathic pain.

12. The method according to claim 10, wherein the composition comprises 0.1 mg or more of the active ingredient.

13. The method according to claim 10, wherein the composition is in a dosage form of an ointment.

* * * * *